United States Patent [19]

Diddams et al.

[11] Patent Number: 5,051,390

[45] Date of Patent: Sep. 24, 1991

[54] CHEMICAL PROCESS AND CATALYST TO BE USED THEREIN

[75] Inventors: Paul A. Diddams, Walton-on-Thames; Ian R. Little, Hampton Hill; Steven R. Wade, Chertsey, all of United Kingdom

[73] Assignee: The British Petroleum Company, p.l.c., London, England

[21] Appl. No.: 419,580

[22] Filed: Oct. 10, 1989

[30] Foreign Application Priority Data

Oct. 18, 1988 [GB] United Kingdom ............... 8824382

[51] Int. Cl.$^5$ .............................................. B01J 37/03
[52] U.S. Cl. .................................... 502/234; 502/241
[58] Field of Search ................................ 502/234, 241

[56] References Cited

U.S. PATENT DOCUMENTS

| | | | |
|---|---|---|---|
| 2,265,389 | 12/1941 | Melaven et al. | 502/241 |
| 2,463,508 | 3/1949 | Bates | 502/241 |
| 3,983,055 | 9/1976 | Mitchell et al. | 502/241 |
| 4,086,261 | 4/1978 | Mitchell et al. | 260/449 |
| 4,443,649 | 4/1984 | Jones et al. | 585/500 |
| 4,523,050 | 6/1985 | Jones et al. | 585/500 |
| 4,629,718 | 12/1986 | Jones et al. | 502/241 |

FOREIGN PATENT DOCUMENTS 0283379 3/1988 European Pat. Off. .
2426698 12/1975 Fed. Rep. of Germany .
2375175 7/1978 France .

*Primary Examiner*—Carl F. Dees
*Attorney, Agent, or Firm*—Nixon & Vanderhye

[57] ABSTRACT

A process for the preparation of a cogel catalyst comprises preparing an aqueous solution containing a soluble compound of an alkali or alkaline earth metal, a soluble metal compound which is thermally decomposable to a metal oxide capable of converting methane to higher hydrocarbons and a hydrolysable silane under such conditions that a homogenous cogel is formed. The cogel catalyst is effective for oxidizing methane to higher hydrocarbons and exhibits greater selectivity and lasts longer than conventional prior art catalysts. A process for using the cogel catalyst to effect oxidation of methane is also described.

9 Claims, No Drawings

CHEMICAL PROCESS AND CATALYST TO BE USED THEREIN

The present invention relates generally to a process for converting methane to hydrocarbons and in particular to the oxidative coupling of methane to higher hydrocarbons in the presence of cogel catalysts. The invention also relates to novel cogel catalysts useful in the performance of the aforesaid process.

The oxidative coupling of methane to produce higher hydrocarbons, for example ethylene, has been extensively studied in recent years. An extensive patent literature covering a large variety of catalysts has accumulated as a result. Oxides of manganese, tin, iridium, germanium, lead, antimony and bismuth have been found particularly useful as catalysts in the oxidative coupling process. The use of such catalysts is described, for example, in U.S. Pat. Nos. 4,443,649; 4,444,984; 4,443,648; 4,443,645; 4,443,647; 4,443,644 and 4,443,646.

Amongst the more promising catalysts are those based on a manganese oxide, as described for example in U.S. Pat. Nos. 4,443,649; 4,544,787; 4,547,608; 4,650,781 and 4,523,050. It is known from, for sxample U.S. Pat. Nos. 4,449,322 and 4,523,049, to use alkali or alkaline earth metals as promoters for manganese oxide-containing catalysts. It is also known from U.S. Pat. No. 4,544,784 that at least one halogen component may be incorporated as a promoter into a contact solid comprising a reducible metal oxide, for example a manganese oxide. In an alternative embodiment of the aforesaid patent, at least periodically the reducible metal oxide and/or the reduced metal oxide is contacted with a halogen source.

Finally, our copending UK application No. 8724373 (BP Case No. 6816) filed on 17th October, 1987 discloses a process for the conversion of methane into higher hydrocarbons by contact at a temperature in the range from 500° to 1000° C. with a molecular oxygen-containing gas and a contact solid comprising a manganese oxide characterised in that at least one of the elements tin, titanium, tungsten, tantalum, silicon, germanium, lead, phosphorus, arsenic, antimony, boron, gallium, iridium, a lanthanide or an actinide is incorporated therein.

A problem sought to be overcome by the inventions of most of the aforesaid patents is that of increasing the methane conversion and selectivity to desirable products, for example ethylene, to values consistent with an economically viable process. Another problem associated with perhaps the majority of the aforesaid prior art catalysts is that although the catalysts may exhibit an initially high activity, this activity declines rapidly with time on stream and can not be restored by reactivation treatments performed on the catalysts.

We have made progress in solving both the aforesaid problems by using a catalyst prepared by a cogelation technique.

Accordingly, the present invention provides a process for the preparation of a cogel catalyst which comprises preparing an aqueous solution containing (a) a soluble compound of an alkali or an alkaline earth metal, (b) a soluble compound of a metal which is thermally decomposable to a metal oxide, capable of converting methane into higher hydrocarbons, and (c) a hydrolysable silane under conditions such that a homogenous cogel is formed.

A preferred method of obtaining a catalyst useful in the performance of the invention comprises the steps of:

(A) mixing an aqueous solution of a soluble salt of an alkali or an alkaline earth metal with a solution of a soluble compound of a metal thermally decomposable to a metal oxide, which metal oxide is capable of converting methane into higher hydrocarbons, (B) adding to the mixture obtained in step (A) a solution in a hydroxylic solvent of a hydrolysable silane, (C) maintaining the mixture obtained in step (B) under such conditions that the mixture forms a cogel, avoiding the formation of precipitates or particles.

(D) drying the cogel obtained in step (C), and (E) calcining the dry cogel obtained in step (D).

The alkali or alkaline earth metal compound and the catalytic metal compound are employed in solution. Suitably, the solution may be an aqueous solution or an aqueous/hydroxylic solvent solution.

Suitably the alkali or alkaline earth metal is one or more of lithium, sodium, potassium, caesium, rubidium, calcium, magnesium, strontium or barium and is preferably sodium. The metal is employed in the form of a soluble compound, which may suitably be a salt of the metal, for example a halide. Preferred is sodium chloride.

Suitably, the metal oxide which is capable of converting methane into higher hydrocarbons is an oxide of one or more of the metals manganese, lanthanum, titanium, zirconium, vanadium, chromium, molybdenum, tungsten, iron, cobalt, nickel, copper, zinc, cadmium, cerium, praseodymium, samarium, lead, tin or bismuth. A preferred metal is manganese. The compound of the metal thermally decomposable to the metal oxide is suitably a salt of the metal, for example a nitrate or carboxylate.

The alkali or alkaline earth metal compound and the catalytic metal compounds may be added as separate solutions or as a single solution.

The hydrolysable silane may suitably be an alkoxy silane.

A preferred class of alkoxy silanes are tetraoxy silanes, most preferred where the alkoxy groups are independently $C_1$ to $C_{10}$ alkoxy groups, most preferred are $C_1$ to $C_4$ tetraalkoxy silanes including tetramethoxy silane, tetraethoxy silane and the like.

Preferably the hydrolysable silane is added as a solution in a hydroxylic solvent. Suitable hydroxylic solvents include alkanols, for example $C_1$ to $C_{10}$ alkanols. A preferred alkanol is that corresponding to the alkoxy group.

It is preferred that the total amount of solvent employed is the minimum consistent with maintaining the homogeneity of the mixture, whilst avoiding any precipitation.

The mixture is preferably thoroughly homogenised, suitably by stirring.

The mixture is maintained under conditions such that there is formed a cogel. A cogel is defined as a polymeric, transparent non-particulate gel. Suitably the mixture is maintained at elevated temperature, for example a temperature just below the boiling point of the mixture, for a period such that cogelation is essentially complete.

It is preferred to dry the cogel so-obtained, suitably by heating at a temperature in the range from 100° to 175° C.

Finally, it is preferred to calcine the dried gel, suitably by heating at a temperature in the range from 100° to 800° C., typically at about 400° to 500° C.

It is preferred to purge the mixture before and/or during gelation with an inert gas, for example nitrogen.

It will be appreciated that it may be possible to combine the drying step (D) and the calcination step (E) into a single step and that the single step may be performed prior to use in the process for converting methane into higher hydrocarbons or 'in situ' as a preliminary to the conversion.

A preferred catalyst is comprised of a NaCl, MnOx (preferably $Mn_3O_4$) and $SiO_2$ cogel.

The methane can be substantially pure methane or may be mixed with other gaseous paraffinic hydrocarbons, for example ethane, propane or butane. Inert diluents, for example argon, helium, or nitrogen may also be employed if desired. Methane is preferably contacted continuously with the catalyst.

There is also fed a molecular oxygen-containing gas, which may be, for example, air or an air/oxygen mixture. Substantially pure oxygen may also be used as the oxygen-containing gas. The molecular oxygen-containing gas may be fed either continuously or intermittently.

A suitable composition of the methane/oxygen-containing gas mixture at atmospheric pressure is a molar ratio of methane to oxygen of from 1.1 to 50 times the stoichiometric ratio of methane/oxygen for complete combustion to carbon dioxide and water. These limits are extendable if operation at pressures greater than atmospheric are envisaged or if the feed gases are preheated. It is preferred to operate at high methane to oxygen ratios within the aforesaid range because higher selectivities to $C_2$ hydrocarbons are obtained, though methane conversions are generally lower. Preferably, conditions are chosen which maximise the selectivity to $C_2+$ hydrocarbons and the methane conversion.

The process is operated at a temperature in the range from 500° to 1000° C., preferably from 700° to 800° C. The pressure may suitably be in the range from 0 to 10 MPa, preferably from 0.1 to 3 MPa bar. The Gas Hourly Space Velocity (GHSV) as measured at STP may suitably be in the range from 100 to 100,000 $h^{-1}$, preferably from 600 to 5000 $h^{-1}$.

The catalyst may be employed in the form of a fixed bed, a fluidised bed, a particulate bed or a recirculating bed, or in any other form.

The process is preferably operated continuously.

It has been found that using catalysts prepared by the aforesaid gelation method as compared with catalysts prepared by other catalyst preparation methods, for example impregnation, higher initial methane conversions and selectivities to ethylene and higher hydrocarbons can generally be achieved. However, the catalyst activity and selectivity may decline in a similar manner to prior art catalysts. However, and this is a major advantage of the cogel catalysts as hereinbefore described, the decline in activity and selectivity can be substantially arrested or retarded by cofeeding a source of halogen.

It is therefore preferred to cofeed in the gaseous phase a source of halogen. The amount of the halogen source fed may suitably be less than about 2% vol/vol, preferably less than 1% vol/vol. Suitable sources of halogen include fluorine, chlorine, bromine or iodine and compounds thereof. Preferably the source of halogen is either chlorine or bromine or a compound thereof. Especially suitable are the hydrogen halides, for example hydrogen chloride or hydrogen bromide, of which hydrogen chloride is preferred. It is believed to be essential for maximum catalyst life for the source of halogen to be fed continuously during continuous operation of the process. Attempts to regenerate a cogel catalyst after use in a process not utilising a halogen co-feed have so far been unsuccessful, as have similar attempts on prior art catalysts. It is believed, though we do not wish to be bound in any way by theory, that in the absence of a source of halogen a silica-rich outer layer forms on the cogel catalysts as hereinbefore described sealing off the catalyst and leading to loss of activity and regenerability.

It has also been found that domain size is a factor in determining the activity and selectivity of cogel catalysts as hereinbefore described. Thus, for $NaCl/Mn_3O_4/SiO_2$ catalysts optimum catalyst activity and selectivity is observed when the largest area of inhomogeneity is less than about 250 $\mu m^2$, with the major portion of the surface having domain sizes of about 5 $\mu m^2$, or less.

Accordingly, the present invention also provides a catalyst for use in the process of the present invention which catalyst comprises an alkali metal halide, a manganese oxide and silica prepared via a cogel wherein the largest area of inhomogeneity is less than about 250$\mu m^2$ and the major portion of the surface has domain sizes of 5 $\mu m^2$ or less.

The domain size may suitably be determined by EDAX analysis in combination with SEM photographs.

Preferably the alkali metal halide is sodium chloride.

Preferably the manganese oxide is trimanganese textraoxide.

The cogel catalyst is preferably obtained by the method as hereinbefore described.

The process and catalyst of the present invention will now be further illustrated by reference to the following Examples.

(1) PREPARATION OF CATALYSTS

Example 1

Cogel Catalyst (NaCl, $MnO_x/SiO_2$)

Sodium chloride (NaCl, Fisons A. R. Grade) (8.9 g) and water (50 ml) were added to manganous nitrate hexahydrate solution [$Mn(NO_3)_2.6H_2O$; 50 wt % aqueous solution; BDH GPR Grade] (44.9 g). After the sodium chloride had dissolved, the solution was added to a mixture of tetraethoxysilane [$Si(OCH_2CH_3)_4$; BDH GPR Grade] (104.0 g) and ethanol (100 ml). The mixture was stirred magnetically and a further portion (150 ml) ethanol was added. A nitrogen purge (500 ml minute$^{-1}$) was introduced into the mixture, which was then heated just below its boiling point with rapid stirring until gel formation occurred.

The resulting gel was air-dried in a pre-heated, well ventilated oven (150° C., 30 minutes) and spread thinly (about 10 mm deep) on to a silica tray and air-calcined in a pre-heated furnace (400° C., 4 hours followed by 500° C. for 1 hour).

The calcined catalyst was crushed and sieved (355–600 um).

Example 2

Cogel Catalyst [NaCl(Mn,Fe)O$_x$/SiO$_2$]

A cogel catalyst additionally containing 0.5 wt % iron was prepared in a similar manner to that described in Example 1.

Comparison Test 1

Impregnated Catalyst (NaCl. MnO$_x$/SiO$_2$)

Manganese dioxide (MnO$_2$; BDH GPR Grade) was heated in air (1000° C., 8 hours) to produce Hausmanite (Mn$_3$O$_4$). Hausmanite (Mn$_3$O$_4$) (54.92 g) was mixed thoroughly with quartz dust (SiO$_2$ washed with conc. HCl, rinsed and dried thoroughly; less than 355 um) (62.68 g) in a solution of sodium chloride (NaCl, Fisons A. R. Grade) (14.03 g) in water (20 ml). The slurry was air-dried (100° C., 18 hours), pressed (10 tons), crushed and sieved (355–600 um).

This is not a catalyst according to the invention and is included for comparison purposes only.

(II) CATALYST TESTING

Example 3

The cogel catalyst of Example 1 was tested for the conversion of methane to higher hydrocarbons.

5 ml catalyst was placed in a 14 mm internal diameter silica-lined tube. A 2:1 by volume mixture of methane:oxygen was passed over the catalyst at a GHSV of 1200h$^{-1}$, the tube being supported in a furnace at 750° C.

The results are given in Table 1.

TABLE 1

| Time on Stream (minutes) | Conversion (%) CH$_4$ | O$_2$ | Selectivity (% C-mol) C$_2$$^+$ | Yield (% C mol) C$_2$$^+$ |
|---|---|---|---|---|
| 210 | 49.3 | 100.0 | 55.4 | 27.3 |
| 345 | 47.8 | 99.7 | 52.7 | 25.2 |
| 530 | 45.8 | 98.4 | 48.9 | 22.4 |
| 580 | 41.0 | 95.0 | 42.3 | 17.4 |
| 775 | 19.3 | 46.5 | 40.8 | 7.9 |

The results presented in Table 1 demonstrate that although the catalyst has a high initial activity and selectivity, it deactivates with time on stream.

Example 4

The cogel catalyst of Example 1 was tested for the conversion of methane to higher hydrocarbons using an HCl cofeed.

5 ml catalyst was packed in a 14 mm internal diameter silica-lined tube. A 2:1 by volume mixture of methane:oxygen was passed over the catalyst at a GHSV of 1200h$^{-1}$. Hydrogen chloride as (HCl) at a rate of 0.5–1.0 m/minute$^{-1}$ was fed along a central silica tube (6 mm internal diameter) packed with silica wool into the bed 10 mm below the top of the bed (bed length 7 cm, holes 6 cm from bed base). The tubs assembly was supported in a furnace at 750° C.

The results are given in Table 2.

TABLE 2

| Time on Stream (minutes) | Conversion (%) CH$_4$ | O$_2$ | Selectivity (% C-mol) C$_2$$^+$ | Yield (% C-mol) C$_2$$^+$ |
|---|---|---|---|---|
| 45 | 49.5 | 100.0 | 53.2 | 26.3 |
| 150 | 48.5 | 100.0 | 52.8 | 25.6 |
| 390 | 48.4 | 100.0 | 51.8 | 25.1 |
| 510 | 47.9 | 99.9 | 50.3 | 24.1 |
| 925 | 49.7 | 100.0 | 50.5 | 25.1 |
| 1295 | 48.2 | 100.0 | 50.4 | 24.3 |

The results in Table 2 demonstrate the beneficial effect of HCl gas in retarding catalyst deactivation.

Example 5

Example 3 was repeated using an NaCl, MnO$_x$/SiO$_2$ catalyst prepared in a similar manner to the catalyst of Example 1, except that before the methane/oxygen mixture was introduced the catalyst was maintained for 1 hour at 750° C. under flowing nitrogen (100 ml minute$^{-1}$).

The results are given in Table 3.

Comparison Test 2

Example 5 was repeated except that instead of the NaCl,MnO$_x$/SiO$_2$ cogel catalyst there was used the impregnated NaCl,MnO$_x$/SiO$_2$ catalyst of Comparison Test 1.

The results are given in Table 3.

Example 6

Example 5 was repeated except that instead of the NaCl,MnO$_x$/SiO$_2$ cogel catalyst there was used the NaCl,(Mn,Fe)O$_x$/SiO$_2$ cogel catalyst of Example 2.

The results are given in Table 3.

TABLE 3

| Example | Catalyst | Furnace Temp. (°C.) | Maximum Bed Temp (°C.) | Conversion (%) CH$_4$ | O$_2$ | Selectivity (% C-mol) C$_2$H$_4$ | C$_2$H$_6$ | C$_2$H$_2$ | C$_3$$^+$ | CO | CO$_2$ | C$_2$$^+$ | Yield (% C-mol) C$_2$$^+$ |
|---|---|---|---|---|---|---|---|---|---|---|---|---|---|
| 5 | NaCl/MnO$_x$/SiO$_2$ cogel | 750 | 792 | 52.4 | 100.0 | 44.5 | 4.8 | 0.3 | 7.8 | 29.5 | 13.2 | 57.3 | 30.0 |
| CT 2 | NaCl/MnO$_x$/SiO$_2$ impreg. | 750 | 775 | 34.0 | 96.3 | 26.0 | 2.5 | 0 | 5.8 | 9.7 | 55.9 | 34.4 | 11.7 |
| 6 | NaCl/(Mn,Fe)O$_x$/SiO$_x$ cogel | 750 | 789 | 49.0 | 100.0 | 42.2 | 4.1 | 0.5 | 8.5 | 29.4 | 15.4 | 55.2 | 27.1 |
| CT 3 | SiC | 750 | 752 | 5.1 | 16.4 | 2.8 | 17.0 | 0 | 0 | 39.1 | 41.1 | 19.8 | 1.0 |

Comparison Test 3

Example 5 was repeated except that instead of the NaCl, MnO$_x$/SiO$_2$ cogel catalyst there was used silicon carbide (SiC).

The results are given in Table 3.

The results reported in Table 3 demonstrate the superiority of the cogel catalyst (Example 5) as compared with the impregnated catalyst (Comparison Test 2). They also demonstrate that the iron-containing catalyst of Example 6 is comparable with the iron-free catalyst of Example 5 and that SiC is a vastly inferior catalyst to either the impregnated or cogel catalysts.

Example 7

A fresh cogel NaCl,MnO$_x$/SiO$_2$ catalyst prepared by a non-optimised method falling within the invention as hereinbefore described was examined by EDAX. Examination of two SEM photographs obtained showed gross features (greater than 100 μm) where particular elements predominate, e.g. Mn predominates along surface cracks, and many Si-rich areas appear deficient in Mn. There are domains greater than 200 $\mu m \times 20$ $\mu m$ in area which show elemental, and therefore phase, inhomogeneity. This catalyst was tested for the conversion of methane to higher hydrocarbons by the method of Example 3.

The results are given in Table 4.

Example 8

A fresh cogel NaCl, $MnO_x/SiO_2$ catalyst prepared by an optimised method falling within the invention as hereinbefore described was examined by EDAX. Examination of a large scale SEM photograph ($\times 200$) obtained showed none of the cracks as observed in the cogel of Example 7 and EDAX of the surface on a very large magnification ($\times 100$) showed a largely homogeneous elemental distribution. The largest area of inhomogeneity detected was 15 $\mu m \times 15$ $\mu m$, with the greater majority of the surface showing domain sizes of about 2 $\mu m \times 2$ $\mu m$ or less. This catalyst was tested for the conversion of methane to higher hydrocarbons by the method of Example 3.

The results are given in Table 4.

The results presented in Table 4 demonstrate that the cogel catalyst having the higher homogeneity in elemental distribution, i.e. that of Example 8, is the better catalyst.

TABLE 4

| Example | Catalyst | Maximum Bed Temp (°C.) | Conversion (%) | | Selectivity (% C-mol) | | | | | | | Yield (% C-mol) |
|---|---|---|---|---|---|---|---|---|---|---|---|---|
| | | | $CH_4$ | $O_2$ | $C_2H_4$ | $C_2H_6$ | $C_2H_2$ | $C_3^+$ | CO | $CO_2$ | $C_2^+$ | $C_2^+$ |
| 7 | NaCl,$MnO_x$/$SiO_2$ cogel | 784 | 51.0 | 100.0 | 42.5 | 4.3 | — | 7.9 | 33.2 | 12.1 | 54.7 | 27.9 |
| 8 | NaCl,$MnO_x$/$SiO_2$ cogel | 792 | 52.4 | 100.0 | 44.5 | 4.8 | 0.3 | 7.8 | 29.5 | 13.2 | 57.3 | 30.0 |

(III) ANALYTICAL INFORMATION FOR USED COGEL CATALYSTS

SEM photographs (X 310) on the used catalyst of Example 3 showed gross phase separation. This catalyst gives inferior performance and its initial activity can not be recovered by regenerating with HCl after it has deactivated.

An SEM photograph on the used catalyst of Example 4 showed a homogeneous surface. There was no formation of large Mn-rich areas such as those observed in Example 3 and some parts of the catalyst show small NaCl crystals in a homogeneous Mn/Si background showing that the Cl in the catalyst, although being removed in the reaction, is replenished from gas phase HCl.

It is concluded that gaseous cofeed HCl at low levels (less than about 1% v/v) maintains the homogeneous dispersion of Mn and Si in an initially homogeneous surface and directly leads to the catalyst maintaining its high $C_2^+$ yield. In the absence of HCl cofeed the catalyst loses chloride and simultaneously suffers separation of Mn- and Si-rich phases, which can not be reversed by subsequent treatment with HCl. Such a catalyst is irreversibly deactivated and gives inferior $C_2^+$ yields.

(IV) SINTERING OF CATALYSTS

It was observed that cogel NaCl, $MnO_x/SiO_2$ catalyts, such as those prepared by the method of Example 1, do not fuse and were poured out of the reactor after performing the Examples in the same granular form as they were initially introduced therein.

On the other hand, the catalyst prepared by the method of Comparison Test 1 after use in Comparison Test 2 was fused into a solid intractable lump.

We claim:

1. A process for the preparation of a cogel catalyst which comprises preparing an aqueous solution containing (a) a soluble compound of an alkali or alkaline earth metal, (b) a soluble compound of a metal which is thermally decomposable to a metal oxide capable of converting methane into higher hydrocarbons and (c) a hydrolysable silane and thereafter allowing a homogenous cogel to form.

2. A process as claimed in claim 1 wherein said soluble compound of an alkali or alkaline earth metal is a halide.

3. A process as claimed in claim 2 wherein said soluble compound is sodium chloride.

4. A process as claimed in claim 1 wherein said soluble compound of said metal which is thermally decomposable to said metal oxide is a soluble manganese compound.

5. A process as claimed in claim 1 wherein said hydrolysable silane is a tetraalkoxy silane in which the alkoxy groups are independently $C_1$ to $C_4$ alkoxy groups.

6. A process as claimed in claim 5 wherein said hydrolysable silane is added as a solution in a $C_1$ to $C_{10}$ alkanol solvent.

7. A process as claimed in claim 1 comprising the steps
   (a) mixing an aqueous solution of a soluble salt of an alkali or an alkaline earth metal with a solution of a soluble compound of a metal thermally decomposable to a metal oxide, which metal oxide is capable of converting methane into higher hydrocarbons,
   (b) adding to the mixture obtained in step (a) a solution in a hydroxylic solvent of a hydrolysable silane,
   (c) maintaining the mixture obtained in step (b) under such conditions that the mixture forms a cogel, avoiding the formation of precipitaties of particles,
   (d) drying the coel obtained in step (c),
   (e) calcining the dry cogel obtained in step (d).

8. A process as claimed in claim 7 wherein said cogel product is dried and calcined at a temperature between 400°–500° C.

9. A process as claimed in claim 1 wherein the largest area of inhomogeneity in said cogel catalyst is less than 250 $\mu m^2$ and the major proportion of the surface has domain sizes of $5\mu m^2$ or less.

* * * * *